United States Patent [19]

Filson et al.

[11] Patent Number: 5,104,546

[45] Date of Patent: Apr. 14, 1992

[54] PYROGENS SEPARATIONS BY CERAMIC ULTRAFILTRATION

[75] Inventors: James L. Filson, Rockford, Ill.; Ramesh R. Bhave, Cranberry Township, Butler County, Pa.; James R. Morgart, Stillman Valley Township, Ogle County; James M. Graaskamp, Machesney Park, both of Ill.

[73] Assignee: Aluminum Company of America, Pittsburgh, Pa.

[21] Appl. No.: 547,488

[22] Filed: Jul. 3, 1990

[51] Int. Cl.$^5$ .................................. B01D 61/00
[52] U.S. Cl. ............................ 210/650; 210/651; 210/653; 210/500.25; 210/900; 424/601; 427/244; 427/246
[58] Field of Search .................... 427/246, 244, 444; 210/252, 651, 500, 637, 490, 500.2, 23, 22, 323.2, 504, 510, 40, 694, 496, 767, 650, 653, 509; 423/626; 424/601, 450; 136/153; 117/66; 252/313; 264/45.5, 4.3

[56] References Cited

U.S. PATENT DOCUMENTS

| | | |
|---|---|---|
| 2,984,628 | 5/1961 | Alexander et al. ............... 252/313 |
| 3,228,876 | 1/1966 | Mahon ............................... 210/22 |
| 3,331,772 | 7/1967 | Brownscombe et al. ........... 210/23 |
| 3,344,928 | 10/1967 | Kraus et al. ...................... 210/500 |
| 3,449,245 | 6/1969 | Johnson et al. ................... 210/23 |
| 3,497,394 | 2/1970 | Berger .............................. 136/153 |
| 3,537,988 | 11/1970 | Marcinkowsky et al. ......... 210/23 |
| 3,874,899 | 4/1975 | Miszenti et al. ................. 117/66 |
| 3,926,799 | 12/1975 | Thomas et al. .................. 210/23 |
| 3,944,658 | 3/1976 | Yoldas ............................ 423/626 |
| 3,977,967 | 8/1976 | Trulson et al. .................. 210/23 |
| 3,993,751 | 11/1976 | Zinke ............................. 424/601 |
| 4,060,488 | 11/1977 | Hoover et al. .................. 210/433 |
| 4,069,157 | 1/1978 | Hoover et al. .................. 210/433 |
| 4,078,112 | 3/1978 | Bibeau ............................ 427/444 |
| 4,082,661 | 4/1978 | Aoki et al. ....................... 210/40 |
| 4,168,229 | 9/1979 | Chambers ........................ 210/23 |
| 4,251,377 | 2/1981 | Schleinitz ........................ 210/510 |
| 4,356,215 | 10/1982 | Auriol et al. .................... 427/244 |
| 4,412,921 | 11/1983 | Leung et al. .................... 210/500.2 |
| 4,523,995 | 6/1985 | Pall et al. ........................ 210/504 |
| 4,562,021 | 12/1985 | Alary et al. ...................... 264/43 |
| 4,610,790 | 9/1986 | Reti et al. ........................ 210/651 |
| 4,640,774 | 2/1987 | Garcera et al. .................. 210/323.2 |
| 4,652,376 | 3/1987 | Kumaoka ........................ 210/694 |
| 4,698,157 | 10/1987 | Gillot ............................. 210/496 |
| 4,724,078 | 2/1988 | Auriol et al. .................... 210/490 |
| 4,734,208 | 3/1988 | Pall et al. ........................ 210/767 |
| 4,737,323 | 4/1988 | Martin et al. .................... 264/4.3 |
| 4,738,874 | 4/1988 | Berardo et al. .................. 427/246 |
| 4,837,028 | 6/1989 | Allen .............................. 424/450 |
| 4,849,104 | 7/1989 | Garcera et al. .................. 210/323.2 |
| 4,865,742 | 9/1989 | Falletti .......................... 210/637 |
| 4,909,942 | 3/1990 | Sato et al. ...................... 210/651 |
| 4,927,571 | 5/1990 | Huang et al. .................... 264/4.3 |
| 4,929,406 | 5/1990 | Abe et al. ....................... 264/45.5 |

OTHER PUBLICATIONS

Abramson, D. et al., "Depyrogenation of a Parenteral Solution by Ultrafiltration", *Journal of Parenteral Science and Technology*, vol. 35, No. 1, Jan.-Feb., 1981, pp. 3-7.

Baggerman, C. et al., "Endotoxin Removal from Large-Volume Parenterals by Various Adsorbents", *International Journal of Pharmaceutics*, 27 (1985), pp. 17-27.

Bergauer, R. G. et al., "The Removal of Pyrogens from Injection Preparations Containing Organic Solvents", *Technical Informations*, pp. 86-87.

*Biopharm.*, Oct. 1989, vol. 2, #9 (Advertisement).

Chervan, M., *Ultrafiltration Handbook*, Technomic Publishing, Lancaster, Pa. (1986), pp. 246-250.

(List continued on next page.)

*Primary Examiner*—Robert A. Dawson
*Assistant Examiner*—Ana Fortuna
*Attorney, Agent, or Firm*—Douglas G. Glantz

[57] ABSTRACT

The method of the present invention for separating pyrogens includes passing a pyrogen-containing liquid through a zirconium oxide membrane on a ceramic support. The membrane on ceramic support preferably includes a porous sintered zircondium oxide membrane on alpha-alumina support.

18 Claims, 1 Drawing Sheet

OTHER PUBLICATIONS

Gerba, Charles P. et al., "Pyrogen Control by Depth Filtration", *Pharmaceutical Technology*, Jun. 1980, pp. 83–89.

Gillot, J. et al., "New Ceramic Filter Media for Cross-Flow Microfiltration and Ultrafiltration", *AVRIL*, 1986, pp. 1–8.

Giorgio, Robert J., "Considerations in the Design of Hot Circulating Water-for-Injection Systems", *Pharmaceutical Technology*, Dec. 1978, pp. 19–25.

Henderson, Lee W., et al., "Successful Production of Sterile Pyrogen-Free Electrolyte Solution by Ultrafiltration", *Kidney International*, vol. 14 (1978), pp. 522–525.

Leahy, Timothy J. et al., "Validation of Bacterial-Retention Capabilities of Membrane Filters", *Pharmaceutical Technology*, Nov. 1978, pp. 65–75.

McGregor, W. Courtney, "Selection and Use of Ultrafiltration Membranes", *Membrane Separations in Biotechnology*, Marcel Dekker, Inc., New York, pp. 1–36.

Nelsen, Lita L., "Removal of Pyrogens from Parenteral Solutions by Ultrafiltration", *Pharmaceutical Technology*, May 1978, pp. 46, 48, 49, and 80.

Olson, Wayne, P., "How to Evaluate Microporous Filtration of Water", *Industrial Water Engineering*, Jan.-/Feb. 1979, pp. 20–25.

SFEC Brochure, 4 pages.

"Self-Repairing Membranes Hold Promise in Desalting Brackish Water", *Chem. and Eng. News*, Dec. 19, 1966, p. 47.

Wilke, H., "Filtration von Injektionspraparaten im Pharmazeutischen Betrieb", *Pharm. Ind.* 18, pp. 428–440.

Wolber, P. et al., "Depyrogenation of Pharmaceutical Solutions by Ultrafiltration: Aspects of Validation", *Pharmaceutical Technology*, Sep. (1987), 6 pages.

Woog, H. et al., "Sterilfiltration und Entpyrogenisierung von parenteralen Arzneimitteln mit neun asbestfreien Tiefenfiltern", *Pharm. Ind.*, 39, Nr. 12, pp. 1261–1266.

Zimmerman, G. et al., "Pyrogen Elimination from Parenteral Medicines by Means of Molecular Filtration", *Drugs Made in Germany*, 19, (1976), pp. 123–128.

Technical Report No. 7, Parenteral Drug Association, Inc., 1986, Chapters 1–14.

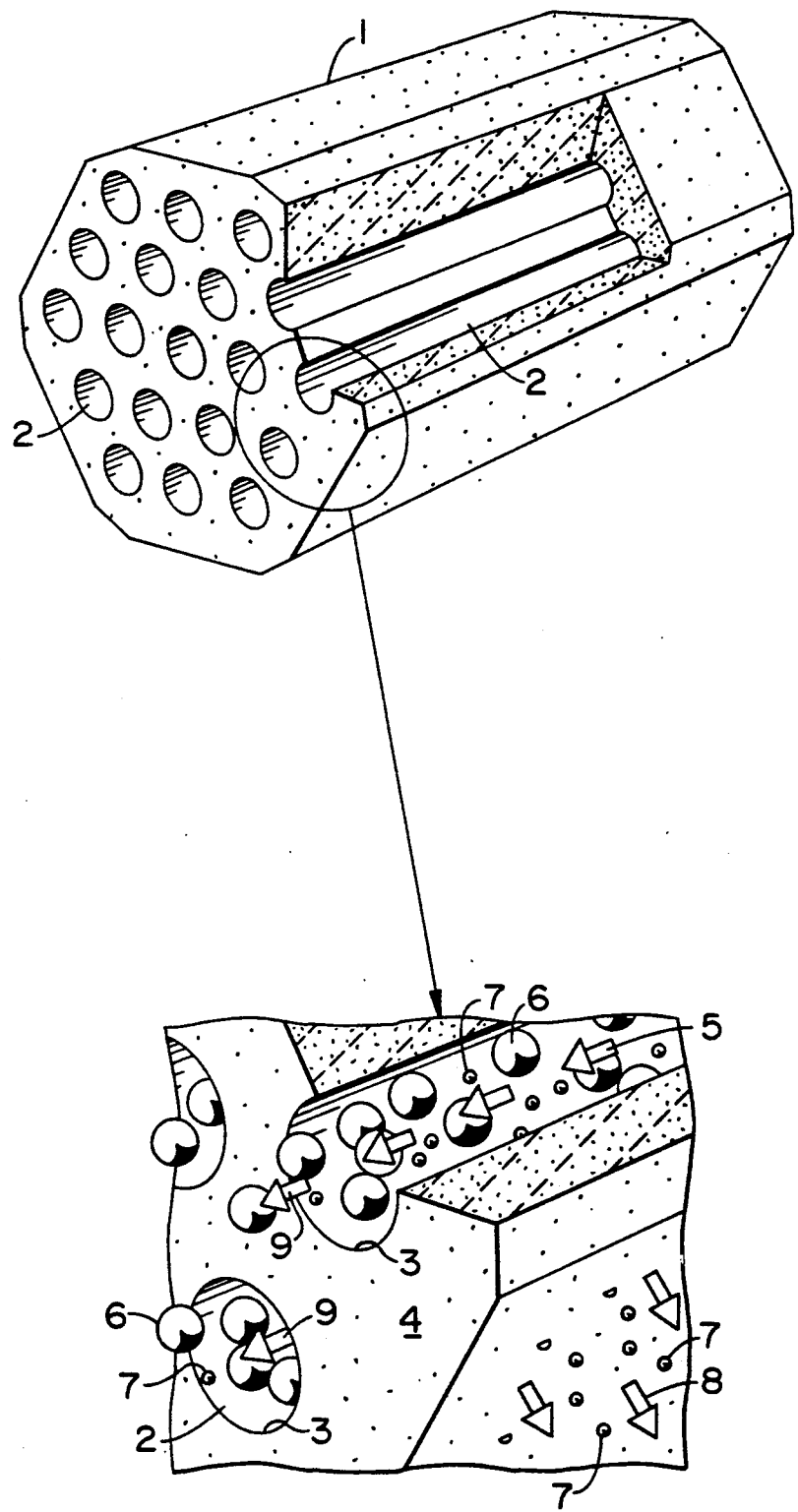

PYROGENS SEPARATIONS BY CERAMIC ULTRAFILTRATION

BACKGROUND OF THE INVENTION

This invention relates to ceramic ultrafiltration and separating life sciences substances.

Asymmetric ceramic filters provide media for microfiltration and ultrafiltration separation processes. These ceramic filters today are becoming recognized for their excellent structural bonding and integrity and are rapidly extending the fields of filtration applications to separations processes performed under extreme conditions of pressure, temperature, and pH.

"New Ceramic Filter Media for Cross-Flow Microfiltration and Ultrafiltration" by J. Gillot et al of the Ceramic Membranes Department of SCT in Tarbes, France, as published in *Filtra 1984 Conference, Oct. 2–4, 1984.* (Apr., 1986) presents alumina membrane-on-support filter media composed of a macroporous support with ceramic membrane layered on multi-channels through the support over channel diameters of 4 or 6 mm. Microfiltration membranes are presented with average pore diameters ranging from 0.2 microns to 5 microns, and ultrafiltration membranes are presented with average pore diameters ranging from 40Å to 1000Å. The membranes on support elements are assembled in modules with filtration surface areas of 0.01 to 3.8 m$^2$. The Gillot et al publication points out characteristics for a support composition of alpha-alumina and for microfiltration membranes composed of alpha-alumina and for ultrafiltration membranes of gamma-alumina.

Ultrafiltration membranes are used for separation processes over a range of filtration size exclusion of generally from about 10 to 20Å to about 1000 to 2000Å. In the context of filtration separations over an entire spectrum of small particle separation processes, reverse osmosis extends from about 1 to 10Å to 20Å, ultrafiltration from about 10Å to 2000Å, microfiltration from about 500Å or 0.05 micron to about 2 microns, and particle filtration from about 1 to 2 microns and up.

Pyrogens are fever-inducing substances and are identified operationally as a substance which, when injected into rabbits in an amount of 10 ml of solution per kg of body weight, raises the body temperature of one rabbit 0.6° C. or a total rise of more than 1.4° C. for three rabbits (USD XIX). Endotoxins are high molecular weight complexes, e.g., molecular weights of about 10,000 up to 100,000 to 200,000 and by some reports up to 1 million, which derive from gram negative bacteria. Bacteria shed their outer membrane into the environment, similarly to a human shedding an outer layer of skin. It is well known that endotoxin causes fever in humans. It appears that the biological activity of endotoxin derives from the lipid portion of the molecule.

Pyrogens are not eliminated by autoclaving because the endotoxin, as represented by the lipopolysaccharide molecule, is resistant to thermal destruction. The lipopolysaccharide molecule is thermally stable, and destruction requires exposure to 250° C. for one-half hour to an hour or more.

Pyrogens can be deactivated, as in depyrogenation, by removal or deactivation. The endotoxin can be treated with an acid or base to deactivate the endotoxin, and this is called depyrogenation by deactivation.

Endotoxins can be removed from a liquid by distillation which is the traditional method for depyrogenation of water and one of two approved methods for the manufacture of non-pyrogenic water, or water for injection. The endotoxin has a large molecular weight compared to the molecular weight of water, so that distillation is effective in rendering the source water non-pyrogenic through distillation processes. The other approved method for manufacture of non-pyrogenic water is reverse osmosis.

Endotoxins can be removed based on molecular size exclusion through reverse osmosis. Reverse osmosis membranes are exclusion membranes but require pressures and structures which make processing difficult because of the small pore size of the reverse osmosis membranes. Moreover, lower molecular weight substances such as salts are excluded by reverse osmosis and this becomes a drawback in forming non-pyrogenic parenteral solutions containing certain salts.

Certain drawbacks are associated with prior conventional processes for pyrogen removal, including distillation, reverse osmosis, and adsorption by asbestos or other media. Distillation processes are highly capital intensive and expensive to operate. Reverse osmosis offers a less expensive method of pyrogen removal but presents substantial problems of cleaning, depyrogenating, and maintaining a non-pyrogenic permeate over extended operational time periods. Distillation and reverse osmosis have the further drawback that neither can be used to depyrogenate parenteral solutions because distillation and reverse osmosis remove the solute with the pyrogen. Asbestos systems now are unacceptable, and other charge media are not sufficiently effective in pyrogen removal.

Ultrafiltration has been identified as a method for pyrogen removal from liquids, polymer structures with pore sizes larger than reverse osmosis membranes but smaller than the microporous filters.

Ultrafiltration membranes concentrate products which are either dissolved or particulate. Through concentration, the product is retained by the filter in a retentate while water and low molecular weight solutes including salts, alcohols, etc., pass through the membrane as a permeate. The concentration operation can be limited by a buildup of retained material at the skin membrane surface. The buildup is called concentration polarization and results in significant resistance to filtration flow.

Ultrafiltration can be an effective means of pyrogen removal because molecular weights of lipopolysaccharides can be on the order of 20,000, for example, and then a 10,000 molecular weight cut-off membrane generally is used to insure high removal efficiency.

However, life sciences applications typically produce a slime on the polymeric membrane, including a film layer which sets up in cross-flow ultrafiltration. Polymeric membranes are particularly susceptible to this buildup of slime because polymeric membranes are not easily cleanable. The polymeric membrane also is degraded by high temperatures or concentrated corrosive chemicals, e.g., such as acids or bases which otherwise would readily clean the membrane.

Polymeric membranes have this drawback not only in cleanability but also in initial sterilization or depyrogenation. To deliver pyrogen-free product, the filter must be pyrogen-free to begin. The membrane also should be sterilizable to eliminate colony-forming bacteria on the membrane structure, and the high thermal stability of lipopolysaccharides makes heat unavailable as the sterilizable, depyrogenating method of choice. Further, the polymeric materials typically cannot be depyrogenated with strong acid (to depyrogenate for initial cleanup). The same factors attributable to polymeric membranes as drawbacks for initial cleaning also apply to regeneration of the polymeric systems also.

It is an object of the present invention to provide a method for depyrogenating a liquid through a filter which can be chemically cleaned initially and on regeneration.

It is a further object of the present invention to provide a method for depyrogenating through a filter which can be acid depyrogenated initially and on regeneration.

It is a further object of the present invention to provide a filter for removing pyrogens from a liquid which can be used over a long period and through numerous regeneration cycles.

It is yet another object of the present invention to provide a method for removing pyrogens from a liquid through a filter having high flux and high permeability.

These and further objects of the present invention will become apparent from the detailed description which follows.

SUMMARY OF THE INVENTION

The method of the present invention for separating pyrogens includes passing a pyrogen-containing liquid through a zirconium oxide membrane on a ceramic support. The membrane on ceramic support preferably includes a porous sintered zirconium oxide membrane on alpha-alumina support.

BRIEF DESCRIPTION OF THE FIGURE

The sole FIGURE shows a schematic representation of a membrane on ceramic support for cross-flow ultrafiltration in accordance with the present invention.

DETAILED DESCRIPTION OF A PREFERRED EMBODIMENT

It has been found that the method of the present invention provides more than a five-log reduction in pyrogen removal combined with surprising and unexpected advantages of high flux and high permeability throughout an extended operating time while providing excellent regenerability through the method employing the zirconia membrane on ceramic support of the present invention.

Pyrogens or endotoxins are terms used generically herein for anything which induces fever in humans. It is necessary that pyrogens are substantially eliminated or separated from a parenteral fluid to safe levels to prevent adverse patient reactions. Pyrogens cannot be eliminated by autoclaving or microfiltration, but are successfully removed by ultrafiltration. Generally, a 10,000 nominal molecular weight cutoff ultrafiltration membrane will provide a two to less than five-log reduction in pyrogen concentration. Prior attempts have not achieved reductions higher than five-log reductions with a one-stage filter. Squibb Institute for Medical Research has reported a 2 log reduction in endotoxin content through a second pass in an ultrafiltration system using a polymeric membrane. Continental Water Systems of San Antonio, Texas reports a 6 log reduction of pyrogenic material but through a two-stage membrane process.

The method of the present invention preferably uses a support material of an alpha-alumina multi-layer support. The alpha-alumina support is a multi-layer structure comprising a sublayer, e.g., such as a sublayer of 0.2 microns pore diameter preferably about an average of 25 $\mu m$ thick, integrally bonded to support an ultrafiltration layer, e.g., a membrane layer which is further supported on a second sublayer, e.g., of about 0.8 microns pore diameter preferably of about an average of 30 to 50 microns thickness, on the other side of the first sublayer. This structure then is further supported on a porous support which has a pore diameter of about 10 to 15 microns and a thickness of about 1.5 to 2 mm.

Raw materials for the outer coating of the membrane include zirconium oxide stabilized with yttrium oxide. These raw materials are mixed with water or alcohol and a suspending agent to form liquid suspensions called slips. The slips are deposited onto the support and are heated to drive off the liquid medium, to burn off the suspending agent, and to sinter the membrane.

Slip preparation from the yttrium oxide-stabilized zirconium oxide begins by mixing the $ZrO_2$ powder with water and organic additives to form a homogeneous suspension. The organic additives, polyvinyl alcohol and ethanol, act as deflocculating agents and also help to adjust the rheological properties of the slip. They are evaporated or burned off later in the manufacturing process. The suspension is then diluted with water.

The slip prepared by the above method is next allowed to flow over the support where it is deposited and dried. The newly-formed layer then is subjected to a heat treatment in an oxidizing atmosphere which removes excess water and alcohol. The heat treatment also oxidizes the organic additives and sinters the $ZrO_2$ particles, thereby fusing them to each other and to the support. Maximum temperatures during the heat treatment vary with the pore diameter desired for the final product, but in all cases the temperatures reach at least 500° C. to ensure all organic additives have been oxidized.

Each finished membrane is tested for compliance with integrity specifications by means of a bubble test used to check for possible point defects. For this test, the supported membrane is enclosed in a suitable container and is immersed in ethanol. Nitrogen gas is injected into the membrane side of the container. The pressure at which nitrogen gas bubbles appear on the support surface of the unit is used to calculate the size of possible defects.

Referring to the sole FIGURE, a schematic diagram is shown for cross-flow ultrafiltration in accordance with the method of the present invention using the ceramic membrane on ceramic support. Ceramic support 1 of alpha-alumina in accordance with the present invention has multi-channels 2 incorporated in the monolithic support material. The channels can be 4 or 6 mm in diameter and are set up in multiple number, e.g., 19 channels per element. A membrane on support is formed inside of the axially oriented channels. Membrane coating 3 provides the ceramic membrane 3 on alpha-alumina support material 4. Feed stream 5 containing pyrogens 6 and water 7 is passed into the channels 2. A back pressure is applied to the feed stream 5 and a permeate stream 8 is passed through the membrane 3 and support material 4 and exits as permeate stream 8. The permeate in this case is primarily water 7. Retentate stream 9 exits the membrane on support element and includes pyrogen 6 and water 7. The membrane 3 preferably has a depth of about 3-5 microns.

The specific membrane on support is provided by SCT in Tarbes, France and is referred to as Membralox ® zirconia ultrafilter.

It has been found that pyrogens can be removed to very high purification levels from water. Pyrogens can be removed with a 5 log reduction in pyrogen concentration in water. A 5 log reduction removes 99.999% of pyrogens by weight.

The method of the present invention includes using zirconium oxide membranes having nominal pore sizes in the range of about 20 to 100Å. By nominal pore size is meant average pore size, e.g., such as about 40Å, including more than about 95% of the pore sizes are within the range of about plus or minus 5% of the nominal pore size, e.g., such as plus or minus 2Å in the case of 40Å nominal pore size. Preferably, the nominal pore size of the zirconium oxide membrane on the support of the present invention is less than or equal to about 50Å.

The ultrafiltration method of the present invention includes passing the pyrogen-containing liquid over the zirconium oxide membrane in a cross-flow or tangential flow over the membrane. By cross-flow or tangential flow is meant that the feed flow is axially channeled and essentially perpendicular to the flow of permeate through the support as shown in the schematic of the sole FIGURE.

It has been found that the method in accordance with the present invention separates pyrogens from a liquid to form a non-pyrogenic fluid. By non-pyrogenic fluid is meant incapable of being detected by the methods available for detecting pyrogens. The methods for detecting pyrogens include a rabbit test and a LAL test. By LAL is meant Limulus Amebocyte Lysate. To achieve an effective utilization of the pyrogen removal process, the initial membrane on support should be depyrogenated prior to operation of the method of the present invention. Depyrogenating can be accomplished by chemically deactivating of the pyrogen, e.g., treatment with a dilute acid, e.g., such as 2% nitric acid or perchloric acid.

The pyrogens referred to in this detailed description of the process of the present invention include pyrogens having a particle size of up to about one micron or aggregate molecular weight of up to about one million, and in one aspect a nominal molecular weight of about 10,000 to 20,000.

The method of the present invention can be described in functional terms also as, for example, by purifying a liquid to remove pyrogens including passing a pyrogen containing liquid through a ceramic membrane having a flux rate or a permeability higher than about 50 L/hr/m$^2$/ atm (transmembrane pressure) to remove pyrogens without substantial fouling of the membrane through a run time of several hours. It has been found empirically through experimental observation and testing that the method provides unexpectedly superior separations characteristics of high flux rate and limited fouling as shown by the observation of flux and permeability through the ceramic membrane on ceramic support in the method of the present invention. The superior characteristics will be described further in the Examples which follow.

EXAMPLE 1

Zirconia membrane on alpha-alumina support referred to as 316SS Membralox ® 1T1-150 Module was provided by SCT in Tarbes, France. The length of the membrane element was 20 cm. The element end seals were a special glass enamel.

The membrane on support element was cleaned with an acidic cleaner to limit corrosion of glass. With other seals, alkaline solutions may be used to clean the membrane element.

Before a test run was made, the system was depyrogenated. This was accomplished with a 2% hot nitric acid solution. Two gallons of a 2% nitric acid solution were prepared in a system feed tank. Using steam and a stainless steel tubing coil immersed in the tank, the solution was slowly heated to 75°-80° C. as it recirculated through the system at 3.7 GPM (1 m/sec). This solution was left to recirculate for approximately 45 minutes during which time the temperature dropped somewhat. During this time, the ΔP (transmembrane) was set at 60 psi and the permeate valve was fully open. This ensured depyrogenation of the module shell side.

After the system depyrogenation period which lasted about 45 minutes, the 2% nitric acid solution was flushed from the system with 3 to 4 gallons of distilled water. Most of the acid was flushed from the system and brought the pH up to about 4.5. A very dilute sodium hydroxide solution then was prepared and added dropwise to bring up the system pH to near neutral value ($\cong$7). When a pH value in the range 6.5-7.0 was reached, another 2 gallons of distilled water were flushed through the system, and the pH was retested with litmus paper (and 2 pH-meters as a cross-check). Any acid still remaining in the shell side was flushed with distilled water (1 gallon was sufficient), and the pH was measured.

When all acid was rinsed and the system was at a pH of 6.5-7.0 (closer to 7.0), a sample of feed and permeate was collected and analyzed for pyrogens. In all tests, it was ensured that the membrane module and the test system was pyrogen-free.

Analytical procedure used the gel-clotting LAL test. The procedure was tested for repeatability and accuracy. Exact concentrations were determined by serial dilutions. Standards and dilutions were made by diluting a known amount of lipopolysaccharides (L-2880, Lot 17F-40191, Sigma Chemicals, St. Louis, Mo.) with sterile, pyrogen-free water that was non-bacteriostatic (the preservative benzyl alcohol used in bacteriostatic water inhibits the test). Thereafter, a small amount was added to a vial containing the gel clot extract. It was mixed, then incubated for 1 hour. The final step was to invert the vial slowly to observe any clotting. If the gel clotted and adhered to the bottom of the vial, the test was positive; if it slid down the side, it was negative. Therefore, concentrations below the sensitivity of the test (0.0125 ng/ml) could not be determined.

The glassware was depyrogenated by heat treatment. It was wrapped in aluminum foil and placed in an oven at 250° C. for 2 hours before use. The pipettes used to transfer the solution were individually wrapped, sterile, disposable pipettes from Fisher Scientific. Samples were taken from depyrogenating the system to be sure it was clean and pyrogen-free. Two samples each of feed side, permeate side, and distilled water were tested prior to each run and all tested negative for pyrogens.

The initial concentration in this Example was 500 ng/ml prepared in fresh distilled water which had already been tested negative for pyrogens. At the end of the run, two samples each were taken from the feed tank, permeate tank, and directly from the permeate line, and tested for pyrogens. The results were:

| Initial Feed: | 500 ng/ml |
|---|---|
| Permeate Sample from permeate collection glass container: | <0.0125 ng/ml |
| Permeate Sample On-line | <0.0125 ng/ml |

TABLE

| | Summary of Results on Pyrogen Rentention With 50Å Membralox ® Zirconia Ultrafilter | | | | | |
|---|---|---|---|---|---|---|
| Example | Pyrogen Load ng/ml Feed (Initial) | Pyrogen Load ng/ml Retentate (Final) | Δ P Transmembrane psi | Water Flux at 20° C., 80 psi L/hr/m² (GFD) (corrected) | LAL Results** (Permeate) ng/ml One-Line | Log Reduction |
| 1 | 500 | 1,000 | 80 | 255 (153) | negative | 4.90 |
| 2 | 1,140 | 1,800 | 80 | 272 (163) | negative | 5.16 |

Module Used: 1T1-150 (element length = 20 cm)
Temperature: 30-40° C.
Cross-Flow Velocity: 1.5 m/s
*Permeability value (L/hr/m²/atm) can be calculated by dividing the water flux value by transmembrane pressure.
**Sensitivity of test 0.0125 ng/ml This shows about a 5 log reduction in the concentration.

Process conditions were held at temperatures of 30°–40° C., a cross-flow filtration velocity of about 1.5 m/sec and a transmembrane pressure was 80 psi. The test lasted for about 45 minutes. Clean water permeability prior to the test run was about 50 L./hr/m²/ atm at 20° C. Average permeability over the duration of the run was 47 L/hr/m²/ atm.

It was found that there was only very low reduction in membrane permeability (to water) from the presence of pyrogens.

The volume of permeate collected was about 2100 ml in a previously depyrogenated glass container. Pyrogen load at the end of the test was about 1000 ng/ml. Initial feed volume was 1 gallon (3.78 l). Two permeate samples were collected on-line, and two samples were collected from the permeate collection glass container. All samples tested for pyrogens with the LAL test, as identified in analytical procedure devised using the gel clotting test, and yielded a negative test, indicating pyrogen concentration below the detection sensitivity of 0.0125 ng/ml.

EXAMPLE 2

Test conditions were changed from Example 1 including a run time of 60 minutes, initial pyrogen load of 1,140 ng/ml, an initial feed of 1.5 gallons (5.68 l).

Average permeability was found to be 50 L/hr/m²/ atm. The clean water permeability before pyrogen testing was 50 L/hr/m²/ atm at 20° C. Accordingly, there was practically no reduction of water permeability in the presence of pyrogens. The concentration of pyrogens in the range of 500–1800 ng/ml appeared not to have any significant affect on permeability.

It was found quite significantly that there was no pore fouling or concentration polarization attributable to pyrogens at molecular dimensions substantially higher than membrane pore size.

The permeate sample on-line was less than about 0.0125 ng/ml.

Test results on pyrogen reduction ability from Examples 1 and 2 are summarized in the Table. The reduction in pyrogen concentration commonly is expressed in terms of the logarithm reduction in pyrogen concentration accomplished by a membrane filter when the filter is challenged by a specific load of pyrogen (expressed in ng/ml).

Log reduction in pyrogen concentration equals $\log_{10}$ [average concentration of pyrogen in retentate (ng/ml) divided by average concentration of pyrogens in the permeate (ng/ml)].

While the invention has been described in terms of preferred embodiments, the claims appended hereto are intended to encompass all embodiments which fall within the spirit of the invention.

What is claimed is:

1. A method of separating pyrogens comprising passing pyrogen-containing liquid through a zirconium oxide membrane on ceramic support, wherein said zirconium oxide membrane has a nominal pore size in the range of about 20Å to 100Å.

2. A method as set forth in claim 1 wherein said ceramic support comprises a porous sintered support.

3. A method as set forth in claim 2 wherein said support comprises a alpha-alumina.

4. A method as set forth in claim 3 wherein said zirconium oxide membrane has a nominal pore size less than or equal to about 50Å.

5. A method as set forth in claim 4 wherein said passing pyrogen-containing liquid through a zirconium oxide membrane comprises a cross-flow or tangential flow over said membrane.

6. A method as set forth in claim 5 wherein pyrogens are separated in an amount of at least about a 5 log reduction.

7. A method as set forth in claim 5 wherein said pyrogens are separated to form a non-pyrogenic fluid.

8. A method as set forth in claim 5 further comprising an initial acid depyrogenating said membrane with nitric acid prior to passing said pyrogen-containing liquid.

9. A method as set forth in claim 8 wherein said liquid comprises water.

10. A method as set forth in claim 9 wherein said pyrogen-containing liquid comprises water containing pyrogen having a particle size of up to one micron.

11. A method as set forth in claim 10 wherein said pyrogens comprise a nominal molecular weight of about 10,000 to 20,000.

12. A method of purifying a liquid to remove pyrogens comprising passing pyrogen-containing liquid through a ceramic membrane having a nominal pore size in the range of about 20Å to 100Å and further having a flux rate or permeability higher than about 40 L/hr/m²/ atm to remove pyrogens without substantial fouling of the membrane through a run time of at least 60 minutes.

13. A method as set forth in claim 12 wherein said ceramic membrane has a nominal pore size in the range of about 20Å to 100Å.

14. A method as set forth in claim 13 wherein said passing comprises a cross-flow or tangential filtration.

15. A method as set forth in claim 14 wherein said pyrogen separation comprises a 5 log reduction in pyrogens in said liquid.

16. A method as set forth in claim 14 wherein said pyrogen separation comprises forming a permeate of non-pyrogenic liquid.

17. A method as set forth in claim 16 wherein said liquid comprises water and said pyrogens comprise life sciences substances having molecular weights in the range of about 10,000 to 20,000.

18. A method of separating pyrogens comprising:
(a) providing an acid depyrogenated, ultrafiltration membrane of porous sintered zirconia oxide having a nominal pore size in the range of about 20Å to 100Å on alpha-alumina support by treating said membrane on support with nitric acid; and
(b) passing pyrogen-containing water by cross-flow or tangential filtration over and through said zirconia oxide membrane on alpha-alumina support to separate pyrogens and form a non-pyrogenic permeate.

* * * * *

UNITED STATES PATENT AND TRADEMARK OFFICE
CERTIFICATE OF CORRECTION

PATENT NO.   : 5,104,546
DATED        : April 14, 1992
INVENTOR(S)  : James L. Filson et al It is certified that error appears in the above-identified patent and that said Letters Patent is hereby corrected as shown below:

On title page, item [54]

| | |
|---|---|
| In the Title: | Change "PYROGENS" to --PYROGEN--. |
| Col. 1, line 1: | Change "PYROGEMS" to --PYROGEN-. |
| In the Abstract, line 5: | Change "zircondium" to --zirconium--. |
| Col. 8, Table, in the right side column under "LAL Results**": | Change "One-line" to --on-line--. |
| In Claim 3, line 2, before "alpha-alumina": | Change "a" to --an--. |

Signed and Sealed this

Twenty-sixth Day of October, 1993

Attest:

BRUCE LEHMAN

Attesting Officer

Commissioner of Patents and Trademarks